US00PP27716P2

(12) United States Plant Patent
Eveleens

(10) Patent No.: US PP27,716 P2
(45) Date of Patent: Feb. 28, 2017

(54) ***HYDRANGEA* PLANT NAMED 'HORTMAFLAM'**

(50) Latin Name: *Hydrangea macrophylla*
Varietal Denomination: HORTMAFLAM

(71) Applicants: Horteve Breeding BV, De Kwakel (NL); Kolster Holding BV, Boskoop (NL)

(72) Inventor: Cornelis Pieter Eveleens, Aalsmeer (NL)

(73) Assignees: HORTEVE BREEDING B.V., Aalsmeer (NL), part interest; KOLSTER HOLDING B.V., Boskoop (NL), part interest ( * ) Notice: Subject to any disclaimer, the term of this patent is extended or adjusted under 35 U.S.C. 154(b) by 11 days.

(21) Appl. No.: 14/756,640

(22) Filed: Sep. 28, 2015

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — June Hwu
(74) *Attorney, Agent, or Firm* — Penny J. Aguirre

(57) ABSTRACT

A new cultivar of *Hydrangea macrophylla* plant named, 'HORTMAFLAM', that is characterized by its inflorescences with sterile florets with sepals that are white in color with dark pink margins (picotee) that retain their picotee color until the antique/autumn phase, and its floriferous blooming habit.

2 Drawing Sheets

Botanical classification: *Hydrangea macrophylla.*
Varietal denomination: 'HORTMAFLAM'.

BACKGROUND OF THE INVENTION

The present invention relates to a new and distinct cultivar of *Hydrangea macrophylla* and will be referred to hereafter by its cultivar name, 'HORTMAFLAM'. 'HORTMAFLAM' represents a new mophead type *Hydrangea*, a deciduous shrub grown for use as a landscape plant and as a cut flower.

The new cultivar was derived from an ongoing controlled breeding program conducted by the Inventor in Boskoop, The Netherlands. The goal of the breeding program is to develop new cultivars of *Hydrangea* with good cut flower qualities with unique flower colors. The objective with this new cultivar was to obtain a plant with sterile floret sepals that were white with a pink edge with good substance. 'HORTMAFLAM' was derived from a cross made in June of 2008 between proprietary plants from the Inventor's breeding program reference no. 07-120-04 (not patented) as the female parent and reference no. 07-036-01 (not patented) as the male parent. 'HORTMAFLAM' was selected in June of 2012 as a single unique plant from amongst the resulting seedlings.

Asexual propagation of the new cultivar was first accomplished by stem cuttings in Boskoop, The Netherlands by the Inventor in August of 2011. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'HORTMAFLAM' as a unique cultivar of *Hydrangea.*

1. 'HORTMAFLAM' exhibits sterile florets with sepals that are white in color with dark pink margins (picotee).
2. 'HORTMACLEPA' exhibits sterile florets with sepals that retain their picotee coloration until the antique/autumn phase.
3. 'HORTMAFLAM' exhibits a floriferous blooming habit.

The female parent of 'HORTMAFLAM', differs from 'HORTMAFLAM' in having a taller plant habit and in being less floriferous. The male parent of 'HORTMAFLAM', differs from 'HORTMAFLAM' in having sterile florets with sepals that open white with a pink edge but quickly change to pink with a darker pink margin. 'HORTMAFLAM' can be most closely compared to the *Hydrangea* cultivars 'HORTMACLEPA' (U.S. Plant patent application Ser. No. 14/756,638) and 'Harlequin' (not patented). 'HORTMACLEPA' is similar to 'HORTMAFLAM' in having picotee colored sepals that do not turn pink until the antique/autumn phase. 'HORTMACLEPA' differs from 'HORTMAFLAM' in having fewer sterile florets per inflorescence with sepals that have a stronger substance and ruffled margins. 'Harlequin' is similar to 'HORTMAFLAM' in having bi-colored flowers. 'Harlequin' differs from 'HORTMAFLAM' in having sterile florets with sepals that are pink with white margins with entire margins (not serrated).

BRIEF DESCRIPTION OF THE DRAWINGS

The accompanying colored photographs illustrate the overall appearance and distinct characteristics of the new *Hydrangea*. The photographs were taken of a three year-old plant of 'HORTMAFLAM' as grown in a 2-liter container in a greenhouse in Boskoop, The Netherlands.

The photograph in FIG. 1 provides a side view of the plant habit of 'HORTMAFLAM' in bloom.

Figure 1:
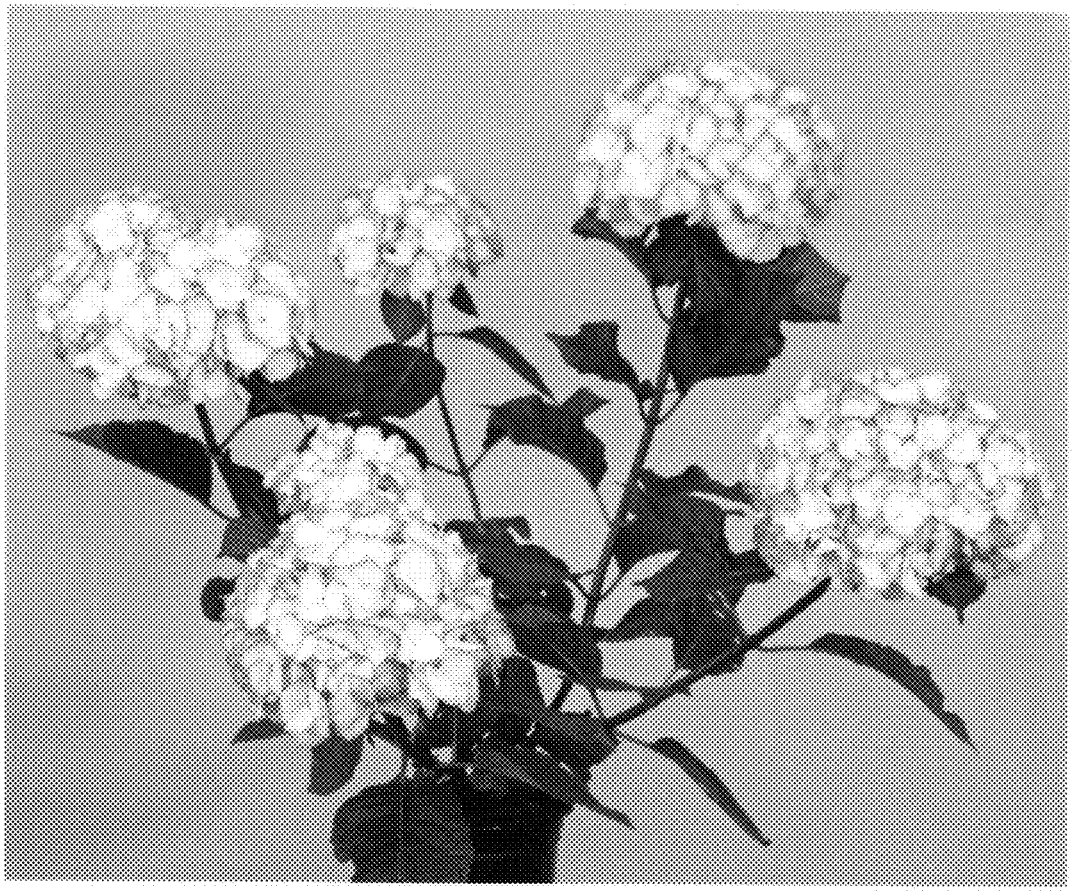
Figure 2:
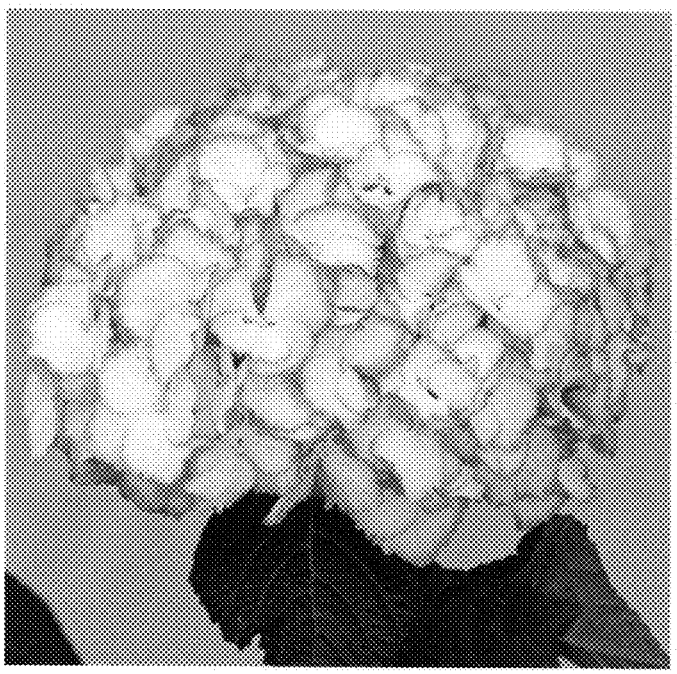

The photograph in FIG. 2 provides a close-up view of an inflorescence of 'HORTMAFLAM'.

Figure 3:
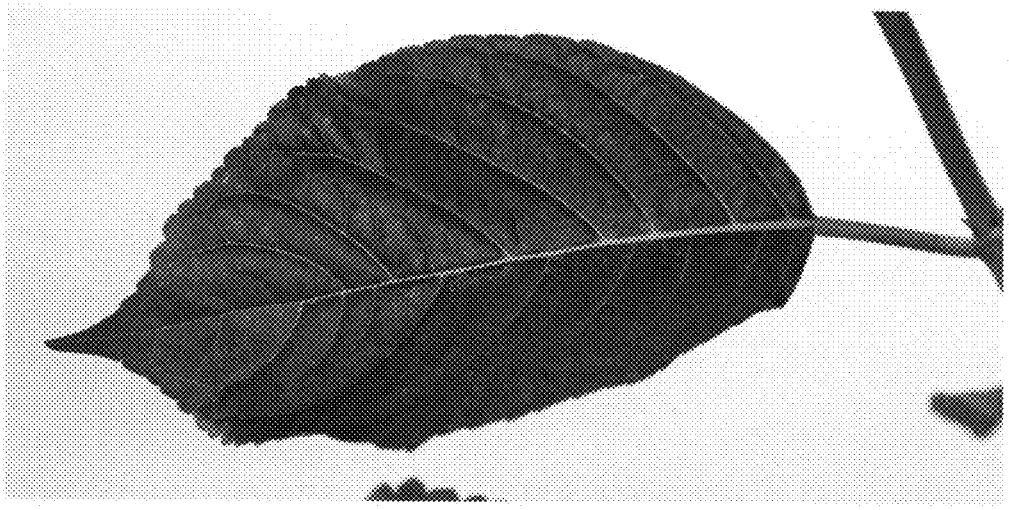

The photograph in FIG. 3 provides a close-up view of a leaf of 'HORTMAFLAM'.

The colors in the photographs are as close as possible with the photographic and printing technology utilized and the color values cited in the Detailed Botanical Description accurately describe the colors of the new *Hydrangea*.

DETAILED BOTANICAL DESCRIPTION

The following is a detailed description of three year-old plants of 'HORTMAFLAM' as grown in a greenhouse in 2-liter containers in May in Boskoop, The Netherlands. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period.*—From May to August in a greenhouse in Boskoop, the Netherlands.

*Plant type.*—Deciduous shrub, mophead type *Hydrangea.*

*Plant habit.*—Broadly upright.

*Height and spread.*—An average of 1 m in height and 60 cm in spread.

*Hardiness.*—At least in U.S.D.A. Zones 5 to 9.

*Diseases resistance.*—No susceptibility and resistance has been observed.

*Root description.*—Fine and fibrous.

*Propagation.*—Stem cuttings.

*Root development.*—An average of 6 months at average air temperatures of 15° to 25° C. to finish a young plant.

*Growth rate and vigor.*—Moderate.

Stem description:

*Stem shape.*—Rounded.

*Stem strength.*—Strong.

*Stem color.*—New growth; 144A, mature growth; 200B to 200D.

*Stem size.*—An average of 42.3 cm in length and 8 mm in diameter.

*Stem surface.*—Glabrous, moderately lenticellate, lenticels; 7 per $cm^2$, an average of 2.5 mm in length and 1 mm in width, 183B in color.

*Stem aspect.*—Held at an average angle of 55° to horizontal.

*Internode length.*—An average of 7.2 cm.

*Branching.*—Low to moderately freely branching with an average of 7 lateral branches.

Foliage description:

*Leaf shape.*—Ovate to broadly ovate.

*Leaf arrangement.*—Opposite.

*Leaf division.*—Simple.

*Leaf base.*—Obtuse to short attenuate.

*Leaf apex.*—Apiculate.

*Leaf margins.*—Serrate.

*Leaf venation.*—Pinnate, color; upper surface 144A and lower surface a blend of 145A and 145B.

*Leaf size.*—An average of 13.7 cm in length and 9.1 cm in width.

*Leaf attachment.*—Petiolate.

*Leaf substance.*—Moderate.

*Leaf surface.*—Both surfaces; glabrous and slightly rugose, lower surface; small tufts of very short soft hairs are present on the vein axils between the main veins and secondary veins with hairs 0.5 mm in length and 157A in color.

*Leaf color.*—Young foliage upper surface; 137A and lower surface; 147B, mature foliage upper surface; a color between N137A and 147A and lower surface; 147B.

*Petioles.*—An average of 3 cm in length and 4 mm in diameter, color; upper surface 144A and lower surface 144A to 144B, both surfaces glabrous and glossy.

Inflorescence description:

*Inflorescence type.*—Terminal panicle, flattened mophead in form comprised of a center region of fertile flowers surrounded by numerous single sterile flowers.

*Lastingness of inflorescence.*—Sterile flowers; persistent for an average of 6 weeks, fertile flowers; an average of 5 days, self-cleaning, flowers dry at maturity.

*Inflorescence number.*—One per lateral stem, floriferous with numerous stems produces per bloom season.

*Inflorescence size.*—An average of 12.6 cm in height and 19.1 cm in diameter.

*Flower number.*—An average of 350 sterile flowers and 90 fertile flowers per panicle.

*Flower fragrance.*—None.

*Flower aspect.*—Sterile flowers; upright to outward, fertile flowers; upright.

*Flower size.*—Sterile flowers; an average of 4 cm in diameter and 2.2 cm in depth, fertile flowers; an average of 4 mm in diameter and 0.5 mm in depth.

*Flower type.*—Rotate.

*Flower buds.*—Sterile flowers; an average of 1 cm in length and 8 mm in diameter, ovate in shape, color; N155D, margins and base 61B, fertile flowers; an average of 4 mm in length and 3 mm in diameter, broad obovate in shape, color; 155C, margins 60D, base 145C.

*Pedicels.*—Sterile flowers; held at an average angle of 30°, an average of 2.6 cm in length and 1.25 mm in diameter, strong, color; NN155D, matte surface covered with short soft hairs an average of 0.1 mm in length and NN155D in color, fertile flowers; held at an average angle of 10° from vertical (0°=vertical), an average of 4 mm in length and 1 mm in diameter, moderate strength, color; NN155D, matte surface is sparsely covered with short soft hairs an average of 0.1 mm in length and NN155D in color.

*Petals.*—Sterile flowers; an average of 4, occasionally 5, rotate arrangement, acute apex, cuneate base, entire margins, ovate and concave in shape, an average of 2 mm in length and 1.5 mm in width, upper side glabrous and matte, lower side glabrous and very slightly glossy, color; upper and lower surfaces when opening; NN155D, margins 60C, upper and lower surfaces when fully opened; petals of sterile flowers are dropped at maturity, color not fading, fertile flowers; an average of 4, rotate in arrangement, ovate and slightly concave in shape, entire margin, acute apex, cuneate base, an average of 2 mm in length and 1 mm in width, upper and lower surface glabrous and dull, color; upper and lower surface when opening; NN155D, margins 60C, when fully opened; petals of flowers are dropped at maturity, color not fading.

*Sepals.*—Sterile flowers; an average of 6, rotate arrangement, broad deltoid to reniform in shape, an average of 2.3 cm in length and 2.8 cm in width, broad to bluntly acute apex, usually with a retuse outer tip, serrated margin, reniform to cordate base, upper surface slightly to moderately rugose, glabrous and matte, lower surface glabrous and matte, color; when opening upper surface and lower surface; NN155D, margins 59D, when fully opened upper surface; NN155D, margins 58A and 58B and lower surface; NN155D, margins 58B to 58C, color fades (antique/autumn phase) to 145C with margins 59D on upper surface and 149D with margins 58B to 58C on lower surface, fertile flowers; an average of 5, rotate in arrangement, ovate in shape, entire margin, acute apex, broadly cuneate base, an average of 1 mm in length and 1 mm in width, both surfaces are glabrous and matte, color; upper and lower surface when opening and when fully opened 145C, color not fading.

Reproductive organs: (Present on sterile and fertile flowers).

*Stamens.*—Sterile flowers; an average of 6, anther; broad kidney-shaped, an average of 0.5 mm in length, and 155D in color, filament; an average of 2 mm in length and NN155D in color, pollen is moderate in quantity and 155A in color, fertile flowers; an average of 8, anther; broad kidney-shaped, an average of 0.5 mm in length and 155D in color, filament; an average of 2 mm, NN155D in color, pollen is moderate and 155A in color.

*Pistils.*—Sterile flowers; an average of 3, an average of 1 mm in length, stigma; club-shaped and NN155C in color, style is an average of 0.5 mm in length and 155A in color, ovary is 155A in color, fertile flowers; an average of 3, an average of 1 mm in length, stigma; club-shaped and NN155C in color, style; an average of 0.5 mm in length and 155A in color, ovary is 155A in color.

*Fruit and seed.*—None observed to date.

It is claimed:

1. A new and distinct cultivar of *Hydrangea* plant named 'HORTMAFLAM' as herein illustrated and described.

* * * * *